(12) United States Patent
Bagaoisan et al.

(10) Patent No.: US 9,855,053 B2
(45) Date of Patent: Jan. 2, 2018

(54) LIGATION CLIP

(71) Applicant: TELEFLEX LIFE SCIENCES UNLIMITED COMPANY, Athlone (IE)

(72) Inventors: Celso Bagaoisan, Union City, CA (US); Suresh Pai, Mountain View, CA (US); James Dreher, Los Angeles, CA (US); Kirk Tamaddon, Calabasas, CA (US)

(73) Assignee: TELEFLEX LIFE SCIENCES UNLIMITED COPMANY, Athlone (IE)

( * ) Notice: Subject to any disclaimer, the term of this patent is extended or adjusted under 35 U.S.C. 154(b) by 607 days.

(21) Appl. No.: 14/353,022

(22) PCT Filed: Oct. 22, 2012

(86) PCT No.: PCT/US2012/061384
§ 371 (c)(1),
(2) Date: Apr. 19, 2014

(87) PCT Pub. No.: WO2013/059826
PCT Pub. Date: Apr. 25, 2013

(65) Prior Publication Data
US 2014/0243862 A1 Aug. 28, 2014

Related U.S. Application Data

(60) Provisional application No. 61/549,740, filed on Oct. 20, 2011.

(51) Int. Cl.
*A61B 17/08* (2006.01)
*A61B 17/122* (2006.01)
*A61B 17/128* (2006.01)

(52) U.S. Cl.
CPC ........ *A61B 17/122* (2013.01); *A61B 17/1285* (2013.01)

(58) Field of Classification Search
CPC ........ A61B 2017/1225; A61B 17/1227; A61B 17/083; A61B 17/08; A61B 17/122; A61B 17/42; A61B 5/150038; A61B 17/32
See application file for complete search history.

(56) References Cited

U.S. PATENT DOCUMENTS

| | | | | |
|---|---|---|---|---|
| 3,825,012 A | * | 7/1974 | Nicoll | A61B 17/122 24/543 |
| 3,867,944 A | * | 2/1975 | Samuels | A61B 17/122 24/23 W |
| 4,345,600 A | * | 8/1982 | Rothfuss | A61B 17/04 606/148 |
| 4,418,694 A | * | 12/1983 | Beroff | A61B 17/122 606/158 |
| 4,450,840 A | * | 5/1984 | Mericle | A61B 17/128 606/143 |
| 4,476,865 A | * | 10/1984 | Failla | A61L 31/04 251/10 |

(Continued)

FOREIGN PATENT DOCUMENTS

| | | |
|---|---|---|
| EP | 0314064 | 5/1989 |
| EP | 0201344 | 12/1989 |

(Continued)

OTHER PUBLICATIONS

Ebbinghaus, M., European Search Report, EP 12842249, Mar. 9, 2015, 7 pages, EPO.

(Continued)

*Primary Examiner* — Amy R Weisberg
(74) *Attorney, Agent, or Firm* — Baker & Hostetler LLP

(57) ABSTRACT

A surgical ligation clip and method of operation are described and include a top jaw member and bottom jaw member joined at a hinge section for movement about the hinge section. The hinge section can be offset or space laterally from one or both of the jaw members. Teeth arrangements and distributions are also described, as well as closing and jaw ends engagement configurations, for example for more easily engaging/piercing connective or other tissue.

34 Claims, 11 Drawing Sheets

(56) References Cited

U.S. PATENT DOCUMENTS

| | | | |
|---|---|---|---|
| 4,487,205 A * | 12/1984 | Di Giovanni | A61B 17/122 251/10 |
| 4,519,392 A * | 5/1985 | Lingua | A61B 17/11 606/151 |
| 4,527,562 A * | 7/1985 | Mericle | A61B 17/122 606/158 |
| 4,550,729 A * | 11/1985 | Cerwin | A61B 17/122 606/158 |
| 4,579,118 A * | 4/1986 | Failla | A61B 17/122 606/158 |
| 4,589,626 A * | 5/1986 | Kurtz | A61M 39/288 251/10 |
| 4,638,804 A * | 1/1987 | Jewusiak | A61B 17/122 606/158 |
| 4,712,549 A | 12/1987 | Peters et al. | |
| 4,716,886 A * | 1/1988 | Schulman | A61B 17/122 30/124 |
| 4,726,372 A | 2/1988 | Perlin | |
| 4,822,348 A | 4/1989 | Casey | |
| 4,834,096 A * | 5/1989 | Oh | A61B 17/122 606/158 |
| 4,936,447 A | 6/1990 | Peiffer | |
| 4,961,499 A | 10/1990 | Kulp | |
| 4,972,949 A | 11/1990 | Peiffer | |
| 5,026,382 A | 6/1991 | Peiffer | |
| 5,046,611 A | 9/1991 | Oh | |
| 5,047,038 A | 9/1991 | Peters et al. | |
| 5,062,846 A * | 11/1991 | Oh | A61B 17/122 606/158 |
| 5,100,416 A | 3/1992 | Oh et al. | |
| 5,104,395 A | 4/1992 | Thornton et al. | |
| 5,112,343 A | 5/1992 | Thornton | |
| 5,127,915 A * | 7/1992 | Mattson | A61B 17/122 606/120 |
| 5,160,339 A * | 11/1992 | Chen | A61B 17/0487 227/902 |
| 5,201,416 A | 4/1993 | Taylor | |
| 5,234,449 A * | 8/1993 | Bruker | A61B 17/122 227/902 |
| 5,279,416 A | 1/1994 | Malec et al. | |
| 5,330,442 A * | 7/1994 | Green | A61B 17/0487 606/151 |
| 5,330,487 A | 7/1994 | Thornton et al. | |
| 5,366,458 A * | 11/1994 | Korthoff | F16B 2/22 606/151 |
| 5,575,802 A * | 11/1996 | McQuilkin | A61F 6/206 128/831 |
| 5,667,516 A * | 9/1997 | Allen | A61B 17/122 606/120 |
| 5,713,912 A * | 2/1998 | Porter | A61B 17/128 606/151 |
| 5,722,982 A * | 3/1998 | Ferreira | A61B 17/083 227/902 |
| 5,810,853 A * | 9/1998 | Yoon | A61B 17/0487 606/151 |
| 5,846,255 A * | 12/1998 | Casey | A61B 17/122 606/120 |
| 5,908,430 A | 6/1999 | Appleby | |
| 5,921,991 A * | 7/1999 | Whitehead | A61B 17/122 606/119 |
| 5,925,052 A * | 7/1999 | Simmons | A61B 17/122 606/108 |
| 6,391,035 B1 | 5/2002 | Appleby et al. | |
| 6,419,682 B1 * | 7/2002 | Appleby | A61B 17/1222 206/339 |
| 6,537,289 B1 | 3/2003 | Kayan et al. | |
| 6,824,547 B2 | 11/2004 | Wilson et al. | |
| 6,863,675 B2 | 3/2005 | Wilson, Jr. | |
| 6,880,699 B2 | 4/2005 | Gallagher | |
| 7,001,412 B2 | 2/2006 | Gallagher et al. | |
| 7,052,504 B2 | 5/2006 | Hughett | |
| 7,131,977 B2 | 11/2006 | Fowler | |
| 7,211,091 B2 | 5/2007 | Fowler et al. | |
| 7,211,092 B2 | 5/2007 | Hughett | |
| 7,316,696 B2 | 1/2008 | Wilson, Jr. et al. | |
| 7,326,223 B2 | 2/2008 | Wilson, Jr. | |
| 7,402,164 B2 * | 7/2008 | Watson, Jr. | A61B 90/92 606/120 |
| 7,585,304 B2 | 9/2009 | Hughett | |
| 8,137,368 B2 | 3/2012 | Kayan et al. | |
| 8,262,639 B2 * | 9/2012 | Mathias | A61M 39/284 604/250 |
| 9,084,596 B2 * | 7/2015 | Stanley | A61B 17/0401 |
| 9,220,507 B1 * | 12/2015 | Patel | A61B 17/1227 |
| 9,445,820 B2 | 9/2016 | Whiting | |
| 2002/0068946 A1 * | 6/2002 | Kortenbach | A61B 1/00073 606/142 |
| 2002/0111640 A1 * | 8/2002 | Krause | A61F 2/0054 606/151 |
| 2004/0059359 A1 * | 3/2004 | Wilson, Jr. | A61B 17/122 606/157 |
| 2005/0165421 A1 * | 7/2005 | Wilson, Jr. | A61B 17/1222 606/151 |
| 2005/0165422 A1 * | 7/2005 | Wilson, Jr. | A61B 17/122 606/151 |
| 2005/0165423 A1 * | 7/2005 | Gallagher | A61B 17/122 606/151 |
| 2006/0217749 A1 * | 9/2006 | Wilson, Jr. | A61B 17/122 606/157 |
| 2007/0083218 A1 * | 4/2007 | Morris | A61B 17/122 606/157 |
| 2007/0118161 A1 * | 5/2007 | Kennedy | A61B 17/122 606/157 |
| 2007/0149989 A1 * | 6/2007 | Santilli | A61B 17/1227 606/157 |
| 2008/0312670 A1 * | 12/2008 | Lutze | A61B 17/122 606/157 |
| 2009/0088783 A1 | 4/2009 | Kennedy et al. | |
| 2009/0171380 A1 | 7/2009 | Whiting | |
| 2009/0240266 A1 * | 9/2009 | Dennis | A61B 17/1227 606/151 |
| 2010/0114131 A1 * | 5/2010 | Rotunda | A61B 17/083 606/157 |
| 2010/0211080 A1 * | 8/2010 | Trivisani | G08B 21/0286 606/120 |
| 2010/0274268 A1 * | 10/2010 | Singh | A61B 17/122 606/157 |
| 2011/0022079 A1 | 1/2011 | Miles et al. | |
| 2011/0295291 A1 * | 12/2011 | Trivisani | A61B 17/122 606/158 |
| 2012/0083803 A1 * | 4/2012 | Patel | A61B 17/122 606/142 |
| 2013/0006271 A1 * | 1/2013 | Vold | A61F 9/007 606/142 |
| 2014/0058411 A1 * | 2/2014 | Soutorine | A61B 17/122 606/142 |

FOREIGN PATENT DOCUMENTS

| | | |
|---|---|---|
| EP | 1 233 705 B1 | 1/2008 |
| EP | 2074954 | 7/2009 |
| JP | 56-151034 A | 11/1981 |
| JP | 61-259652 A | 11/1986 |
| JP | 3-178648 A | 8/1991 |
| WO | WO 2006/102578 | 9/2006 |
| WO | 2012/075532 A1 | 6/2012 |

OTHER PUBLICATIONS

Jung, Soo Hwan, International Search Report, PCT/US2012/061384, dated Mar. 29, 2013, 5 pages, KIPO.

English translation of Notice of Reasons for Rejection issued in Japanese Patent Application No. 2014-537368, dated Sep. 15, 2016.

* cited by examiner

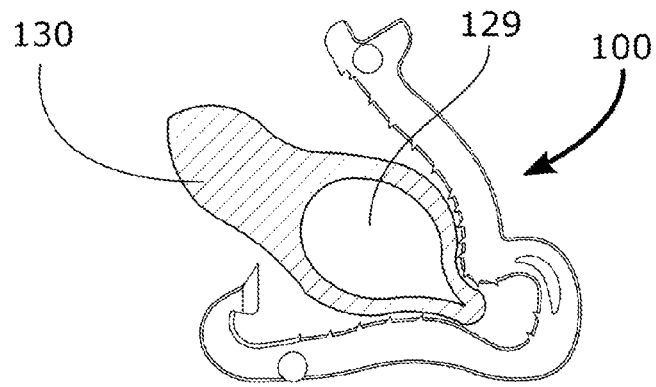
FIG. 5A
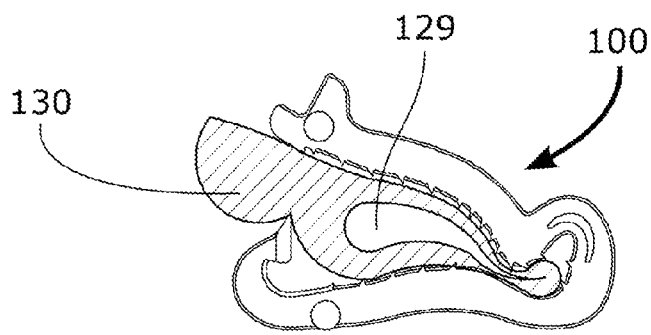
FIG. 5B
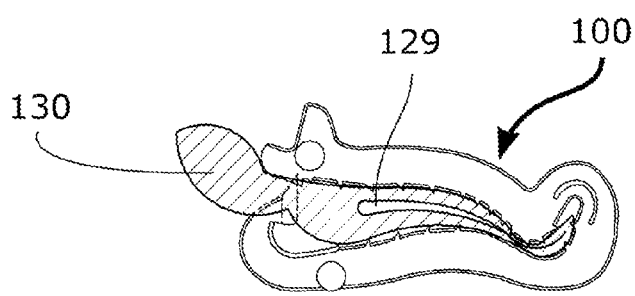
FIG. 5C
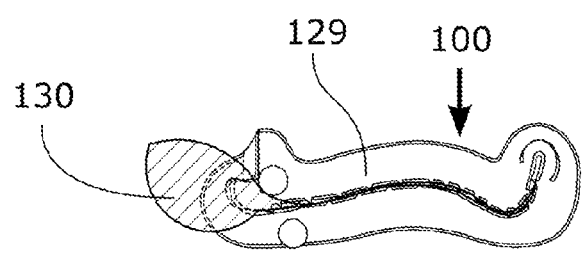
FIG. 5D
FIG. 5

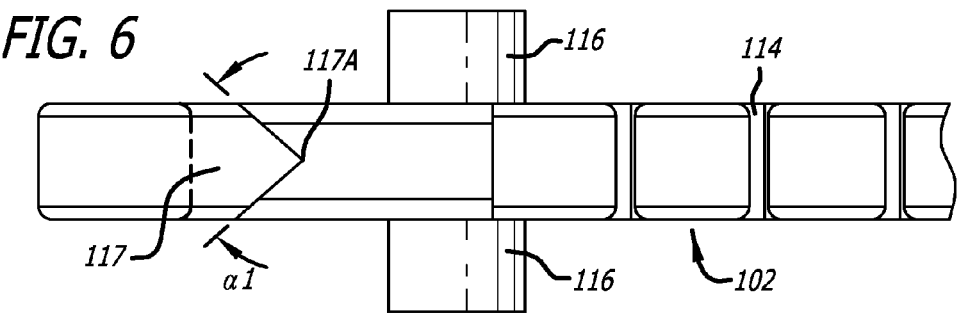
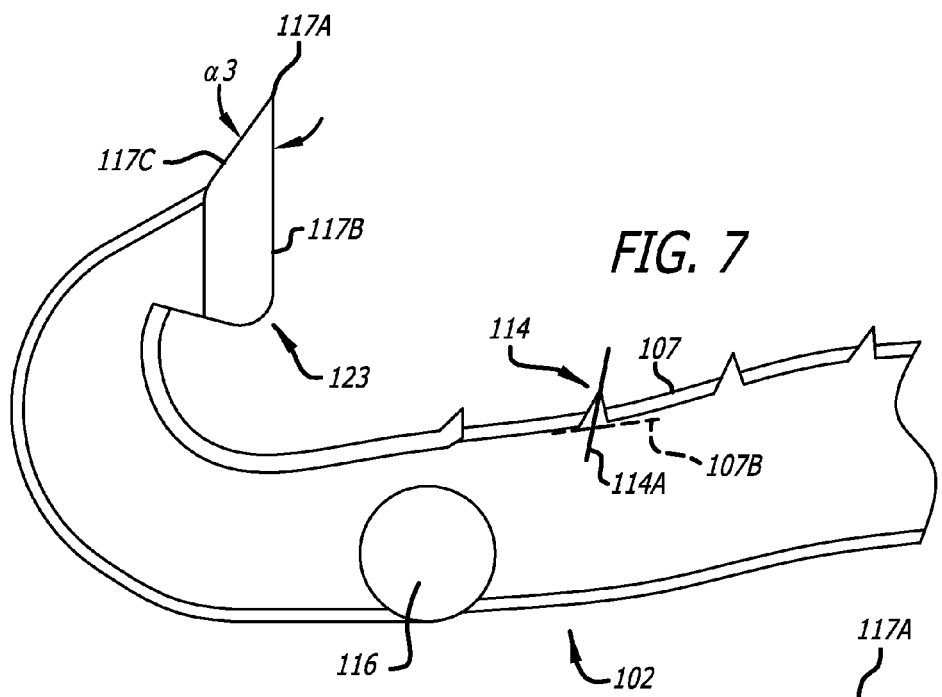
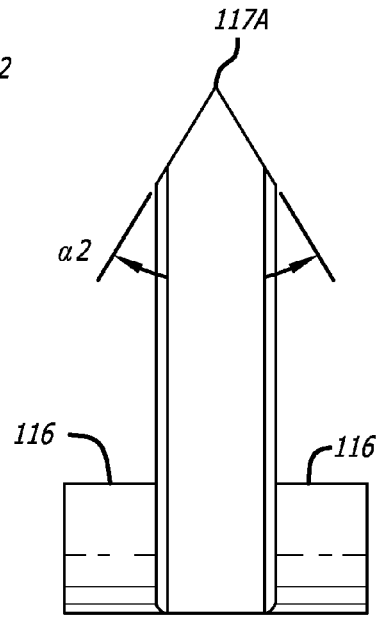

LIGATION CLIP

CROSS REFERENCE TO RELATED APPLICATIONS

This application is a National Stage Filing of International Application No. PCT/US2012/061384, filed Oct. 22, 2012, and claims priority to U.S. Provisional Application No. 61/549,740, filed Oct. 20, 2011.

BACKGROUND OF THE INVENTIONS

Ligation of vessels or other anatomical structures is a common step in a large number of surgical procedures. Traditionally, a ligation procedure comprises the placement of a suture about the target vessel or anatomical structure (e.g. artery, vein, duct, Fallopian tube, etc.) and tying off the suture to close the vessel, conduit or structure. The effective use of sutures to accomplish this procedure relies on the skillful execution of complex knots using a needle and thread. The space and time needed for this process limits the efficacy of suture-based ligation techniques, particularly in endoscopic or laparoscopic surgeries. The restrictions to freedom of movement incumbent in the use of minimally invasive surgical techniques present a significant challenge to the surgeon when ligating target vessels or structures with sutures.

The use of ligation clips in open and endoscopic surgical procedures addresses many of the shortcomings of suture-based ligation. Ligation clips are commonly applied with a tool specifically designed to hold and securely apply the clip to a target vessel or the like. Various types of ligation clips are commercially available, and can be broadly grouped into symmetric or asymmetric designs fabricated from metallic or polymeric materials. The metallic clips are typically symmetric in shape (e.g. U or V shaped) and fabricated from materials including, but not limited to, stainless steel, titanium, tantalum, and alloys thereof. The metallic clips are placed around the target vessel and permanently (i.e. plastically) deformed to close and restrict flow through the target vessel. While functional, the design and material components of metallic clips limit their use under the state of the art. For example, metallic clips cannot be used in patients that may undergo magnetic resonance imaging (MRI) or computed tomography (CT) as the clips can interfere with the signals used in those imaging modalities. Furthermore, since the metallic clips are closed via permanent deformation of the clip itself, an inherent limit is placed on the size vessel a given size of metallic clip can close (i.e. the high magnitude of deformation required to close a metallic clip about a larger diameter vessel may weaken the metal and induce a break or other failure in the structure of the clip) resulting in potentially catastrophic clinical consequences.

Polymeric ligation clips provide an alternative to metallic clips with several important differences. One such difference is the compatibility of polymeric clips with state of the art imaging modalities (e.g. MRI, CT, etc.). For example, polymeric ligation clips are non-magnetic and can be used in patients that will likely undergo MRI in the future. A second difference is in the means of maintaining the clips in closed state about the target vessel. Polymeric ligation clips are not typically plastically deformed about the target vessel; instead, the clips include design features that employ locking or latching mechanisms to hold the clip in a closed state. This offers an advantage over metallic, plastically deformable clips, in that a larger vessel for a given clip size may be closed with a plastic locking clip (as opposed to a plastically deformable clip of similar size), provided the locking mechanism is strong or robust enough to maintain the clip in the closed or securely locked position. Polymeric clips may further be divided into those that are intended for permanent residence in the patient following the surgical procedure and those that are designed to degrade after a specified amount of time post-implantation.

A ligation clip that can pinch or retain the target vessel or tissue or a part thereof, for example into the jaws of the clip prior to the clip reaching the fully closed position, provides a clip that is easier and more reliable to use. A clip that can secure the vessel or tissue in a position close to the hinge or junction of the clip as the jaws close provides for increased utilization of the available clip space. Also, a clip that can draw or pull the pinched vessel or tissue towards the hinge or junction section when the clip is closing and/or retain it there when the clip is fully closed and locked provides a more reliable and useful clip. Furthermore, a ligation clip comprising a robust means of piercing through or penetrating tissue that is attached to the target vessel and may interfere with the closing and/or locking of the ligation clip also improves the use and reliability of ligation clips.

SUMMARY

A ligation clip with an improved means of securing the target vessel or tissue prior to locking the jaws in the closed position is provided. Further disclosed are designs of ligation clips that have increased contact surface length while maintaining a minimal overall length profile of the clip, thereby enabling the ligation of larger vessels or tissues. Examples are also provided for a means of piercing tissue adjacent to a vessel that is disposed between the locking features of the ligation clip, and present an atraumatic form to the tissues surrounding the target upon closure of the ligation clip.

In one example of a ligation clip, the clip includes first and second jaws movably coupled to each other by a flexible portion positioned at proximal portions of the jaws. The flexible portion may be offset from one or both of the first and second jaws. The flexible portion can be positioned relative to the first and second jaws so that the flexible portion is positioned so as to be asymmetric relative to the first and second jaws. In another example, the flexible portion is joined to one of the jaws by an angularly-extending element extending between the flexible portion and the respective jaw. The angularly-extending element may extend at an angle to a longitudinal extent of the jaw, or at an angle to a line that represents an average of the direction in which the jaw extends.

In a further example of a ligation clip, the ligation clip, including one such as the ligation clip described above, includes a jaw having a tooth extending at an angle to a surface on which the tooth is supported. In one example, first and second teeth on a given jaw extend at angles different relative to each other. In another example, the ligation clip includes a jaw having a plurality of teeth and wherein the density of a first plurality of teeth on one portion of the jaw is greater than or equal to zero, and a second density of teeth on another portion of the jaw is greater than the first density of teeth. In another example, a first jaw has teeth distributed according to a first density and the second jaw of the clip includes a density of teeth distributed according to a second density different than the first density.

In a further example of a ligation clip, the clip, including ones such as the ligation clip examples described above, has a first jaw having a lateral extension and wherein the lateral extension includes at least one tooth. The lateral extension may extend at an angle from the first jaw, and in one example, may extend at an approximately right angle to the first jaw. The lateral extension may include a plurality of teeth, and at least one tooth on the lateral extension may be supported at an angle to the surface of the jaw at which the tooth is mounted. In one configuration, the lateral extension has a flexibility substantially the same as that for the first jaw, and where a flexible hinge portion is included in the clip, the lateral extension may have a flexibility less than that of the flexible hinge portion.

In another example of a ligation clip, a ligation clip, including ones such as the ligation clip examples described above, includes a flexible portion having a wall defining an opening into or completely through the flexible portion. In one configuration, the opening extends longitudinally of the clip a distance greater than a widthwise direction. In another configuration, the flexible portion is configured to have different measures of flexibility at different locations within the flexible portion. For example, in the configuration where the flexible portion includes an opening, the opening can extend over an arc when the clip is in an open configuration, and in a further configuration, an opening forming part of the flexible portion extends over an arc. In a further configuration, and opening forming an arc for part of the flexible portion can be defined by adjacent walls wherein one wall forming one side of the arc has a thickness different than another wall forming another side of the arc. In an additional configuration, a ligation clip having a flexible portion with an opening in the form of an arc when the clip is in an open configuration can be formed so that one portion, for example the center, of the arc has a greater flexibility than another portion of the arc.

In a further example of a ligation clip, a ligation clip, including ones such as the ligation clip examples described above, has a jaw with a corner portion within the ligation clip. The corner portion may be partially circular, have an eccentric curvature, or a multiple-surface configuration. In one configuration, the corner portion includes a plurality of teeth on the corner portion, and may include at least one tooth on a first area of the corner portion and a second tooth on a second area of the corner portion, directed in a direction. In another configuration, at least one tooth on the curved surface is oriented in a proximal direction, for example toward a hinge portion of the clip. Where the hinge portion is a flexible hinge portion, the at least one tooth on the curved surface is directed at least partly toward the hinge portion.

In another example of a ligation clip, the ligation clip, including ones such as the ligation clip examples described above, has first and second jaws coupled to each other by a junction portion. The junction portion includes at least one element extending over a first distance at an angle to the first jaw, and the junction portion includes an opening extending over a second distance less than the first distance. In one configuration, the junction portion is offset from the first jaw, and in another configuration, the junction portion may include an arcuate opening. The arcuate opening may define a flexible portion wherein one location in the opening, for example when the clip is in an open and relaxed state, may have a different flexibility than another location in the opening. In another configuration, the clip may include a piercing element at a distal portion of the first jaw and an edge receiver on a distal portion of the second jaw for contacting the piercing element.

In a further example of a ligation clip, the clip, including ones such as the clip examples described above, includes first and second jaws wherein the first jaw includes a piercing element and the second jaw includes a receiver and wherein the receiver includes a surface for receiving part of the piercing element. In one configuration, the piercing element includes a longitudinally extending edge to be received in the edge receiver. In another configuration, the edge receiver includes a channel, for example a straight channel, for receiving a portion of the piercing element. The channel can have a length greater than a length of a piercing element to be received in the channel. In one configuration, the piercing element does not extend beyond an end surface of the receiver. In another configuration, the receiver includes a guide surface for guiding part of the piercing element along a distal portion of the second jaw. The guide surface may be continuous with the receiver.

Methods are also described for using ligation clips. In one example, the forces are applied to first and second jaws of a clip to bring the first and second jaws closer together and moving a proximal portion of the first jaw along a portion of the second jaw. In one configuration, movement of the proximal portion of the first jaw moves adjacent tissue along a surface of the second jaw. In another configuration, teeth on the proximal portion of the first jaw may move tissue adjacent the teeth along a portion of the second jaw lacking teeth. The teeth on the proximal portion of the first jaw may move the tissue adjacent the teeth proximally along a relatively smooth portion of the second jaw.

A ligation clip can be manipulated by applying forces to first and second jaws of the clip and moving the tissue proximally using a proximal portion of the first jaw. In one configuration, the first jaw moves the tissue proximally toward a hinge portion of the clip. In another configuration, tissue is moved by the first jaw proximally and away from the second jaw in the clip.

In a further configuration, a ligation clip can be manipulated by applying forces to first and second jaws of the clip, and deflecting a hinge portion distally of the clip when first and second jaws of the clip are moved toward each other. In one configuration, the hinge portion is positioned offset from the second jaw, and the hinge portion is deflected when a distal portion of the second jaw contacts a distal portion of the first jaw. When the distal portion of the second jaw contacts the distal portion of the first jaw, the distal portions may slide relative to each other, which may cause the hinge portion to deflect. In a further configuration, sliding of the distal portions relative to each other may first cause the end portion to deflect, followed by engagement of the distal portions with each other.

These and other objects, advantages, and features of the inventions will become apparent to those persons skilled in the art upon reading the details of the disclosure as more fully described below.

BRIEF DESCRIPTION OF THE DRAWINGS

The inventions are best understood from the following detailed description when read in conjunction with the accompanying drawings. It is emphasized that, according to common practice, the various features of the drawings are not to-scale. On the contrary, the dimensions of various features are arbitrarily expanded or reduced for clarity. Included in the drawings are the following figures:

FIG. 5 is a series of images depicting the surgical ligating clip of FIG. 1 being applied securely across a target vessel.

FIG. 6 is a top plan view of a distal portion of a bottom jaw in the clip of the example shown in FIG. 1.

FIG. 7 is a side elevation of the portion shown in FIG. 6.

FIG. 8 is a front elevation view of the portion shown in FIG. 7.

DETAILED DESCRIPTION

Figure 1:
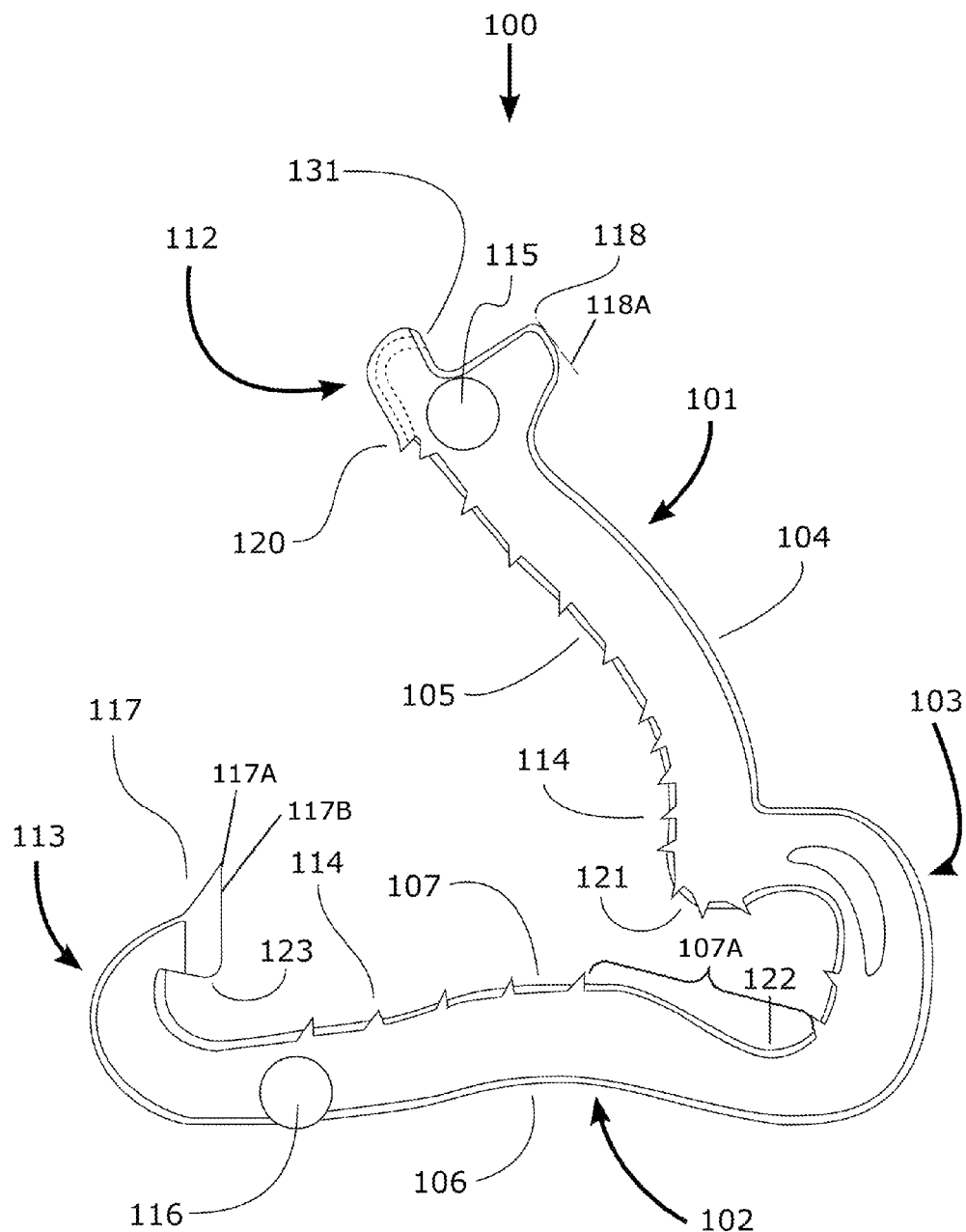
FIG. 1 is a side view of one example of a surgical ligating clip of the present inventions.

Examples of clips and of methods of making and using the clips are described. Depending on what feature or features are incorporated in a given structure or a given method, benefits can be achieved in the structure or the method.

These and other benefits will become more apparent with consideration of the description of the examples herein. However, it should be understood that not all of the benefits or features discussed with respect to a particular example must be incorporated into a tool, component or method in order to achieve one or more benefits contemplated by these examples. Additionally, it should be understood that features of the examples can be incorporated into a clip, component or method to achieve some measure of a given benefit even though the benefit may not be optimal compared to other possible configurations. For example, one or more benefits may not be optimized for a given configuration in order to achieve cost reductions, efficiencies or for other reasons known to the person settling on a particular product configuration or method.

Examples of several clip configurations and of methods of making and using the clips are described herein, and some have particular benefits in being used together. However, even though these apparatus and methods are considered together at this point, there is no requirement that they be combined, used together, or that one component or method be used with any other component or method, or combination. Additionally, it will be understood that a given component or method could be combined with other structures or methods not expressly discussed herein while still achieving desirable results.

It should be understood that terminology used for orientation, such as front, rear, side, left and right, upper and lower, and the like, are used herein merely for ease of understanding and reference, and are not used as exclusive terms for the structures being described and illustrated.

These inventions are not limited to particular examples described, as such may, of course, vary. It is also to be understood that the terminology used herein is for the purpose of describing particular examples only, and is not intended to be limiting, since the scope of the present inventions will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the inventions. The upper and lower limits of these smaller ranges may independently be included or excluded in the range, and each range where either, neither or both limits are included in the smaller ranges is also encompassed within the inventions, subject to any specifically excluded limit in the stated range. Where the stated range includes one or both of the limits, ranges excluding either or both of those included limits are also included in the inventions.

Unless defined otherwise, all technical and scientific terms used herein have the same meaning as commonly understood by one of ordinary skill in the art to which these inventions belong. Although any methods and materials similar or equivalent to those described herein can be used in the practice or testing of the present inventions, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

Figure 2:
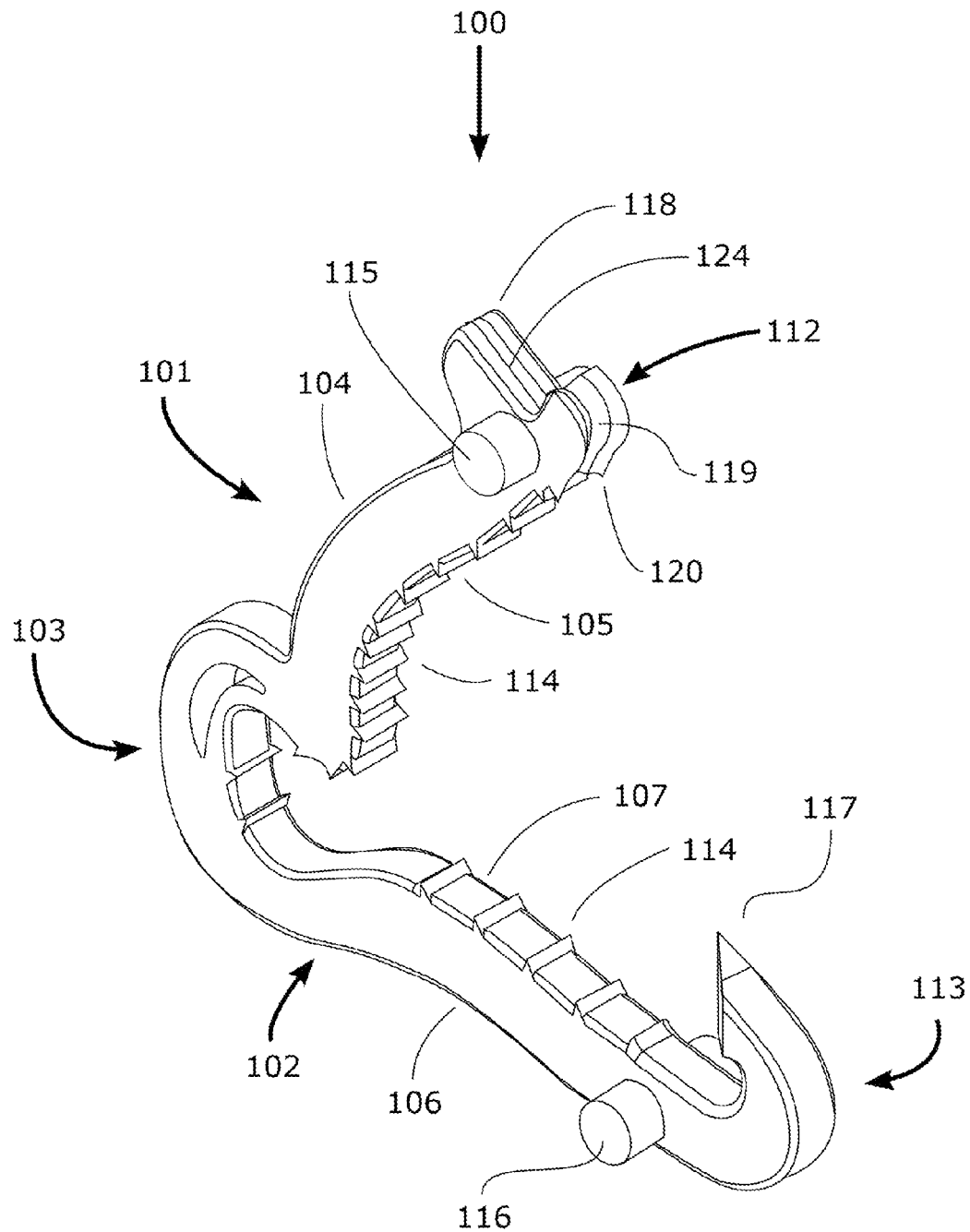
FIG. 2 is an isometric view of the example of FIG. 1.

FIGS. 1 and 2 are side and isometric views, respectively, of one example of a surgical ligation clip of the inventions 100. FIG. 3 is a close up view of the flexible portion of the clip, identified herein as the hinge section 103 of ligation clip 100. The body of clip 100 is comprised of top jaw member 101 and bottom jaw member 102 joined at hinge section 103. jaw members 101 and 102 are formed such that they have complementary curved inner or facing surfaces that mate when the clip is in a closed position, but they can also be substantially straight or take other configurations as desired. In the present examples, top jaw member 101 has an outer surface 104 that is generally convex and an S-shaped inner surface 105. Additionally, the proximal side of the jaw member 101 proximally projects towards the hinge section 103, forming a heel 121 which may be configured with a radius corner. While heel 121 is shown with a radius corner, other atraumatic configurations may be employed such as, but not limited to, chamfers or the like. Bottom jaw member 102 has an outer surface 106 that is generally concave and an S-shaped inner surface 107 that approximately matches or conforms to the profile of the inner surface 105 of top jaw member 101. The proximal side of the bottom jaw member 102 proximally projects towards the hinge section 103, and, in the present example, the jaw transition 122 comprises an inner radius or configuration that matches the corner radius or configuration of heel 121. The distal side of bottom jaw member 102 may also project distally and connect to the piercing element 117 and latch 122. The degree of wave or curvature and the length of dorsal or ventral projection(s) of the aforementioned jaw members 101 and 102 may be varied along the length of a jaw to further extend or lengthen the clamping surface, thereby allowing the clip 100 to ligate a larger vessel without significantly affecting the overall length of the clip 100.

Figure 3A:
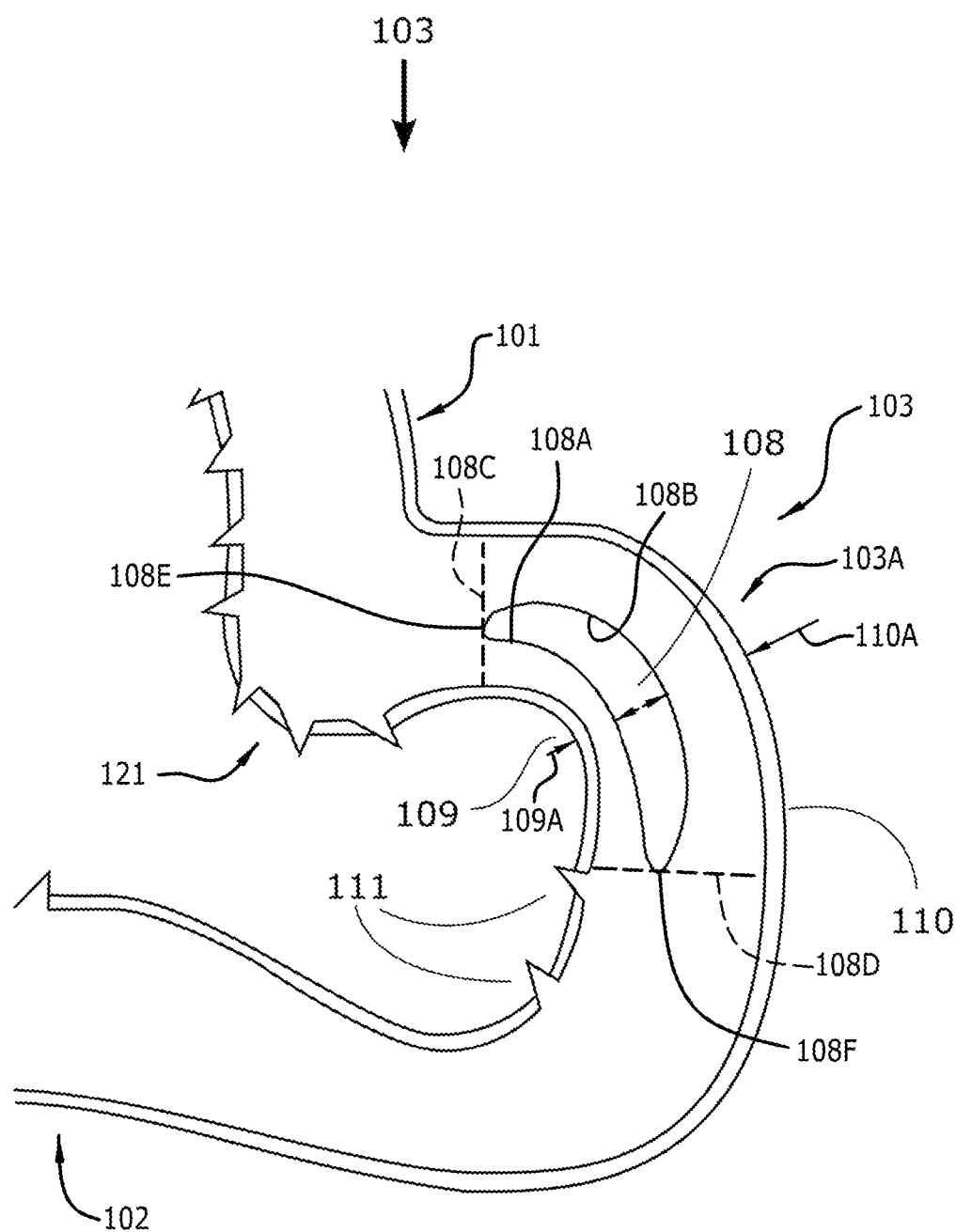
FIG. 3 is a magnified side view of hinge section of the example of FIG. 1.
Figure 3B:
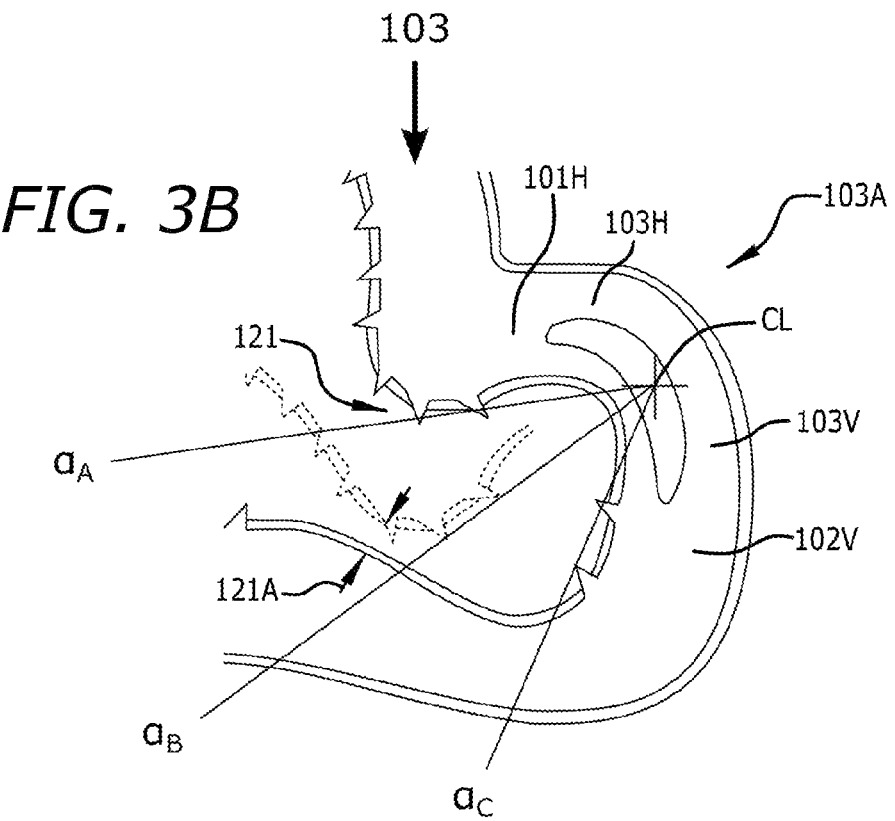

As best shown in FIGS. 3A and 3B, hinge section 103 in the present example is flexible over an extended length. While the hinge section can be considered to have a central pivot point, such as CL as described herein, several of the specific examples described herein are configured so that the hinge section is flexible or bends or pivots over a distributed area, for example with an effective or constructive pivot point, and for example flexible between endpoints of a flexible area (as distinct from inflexible elements pivoting about a pivot axis). In one configuration, the distributed flexing or bending is achieved by the provision of a noncircular opening such as the slot 108 described more fully herein. Conversely, if distributed flexing or bending is not desired, flexing or bending about a single axis can be used while adopting other features of the inventions described herein.

In the examples described herein, the hinge section is offset from the jaw members, for example in a direction of motion of one of the jaw members, for example laterally form the jaw members when the clip is in the closed configuration. The hinge section 103 can be laterally offset from both of the jaw members, for example at ends of respective lateral extensions of each of the jaw members. When the hinge is positioned laterally of both of the jaw members, the hinge can be incorporated at any of a number of selected locations on the lateral extensions of the jaw members, so that the hinge section 103 operates with the jaw members to achieve the desired closing and tissue clasping and tissue moving functions. A hinge section can be formed from a plurality of hinge elements (one or more of the hinge elements having the characteristics of the hinge section described herein. For example, the plurality of hinge elements together or as an assembly may be configured to achieve the desired closing and tissue clasping and tissue moving functions. For a given hinge section, whether a single hinge element or a plurality thereof, the hinge section is taken to be bounded on one end by the termination of a slot as described herein at one end of the section and by the termination of a slot at another end of the section, along with the material in between. In one example, the material in between would be the material between tangent lines 108C and 108D of the slot termination points. Where there is a single slot, as illustrated herein, the hinge section boundary is defined by the terminal ends 108E and 108F of the slot, such as the terminal ends of the slot 108 described herein. Where there are multiple slots each contributing to the hinge function, the hinge section is bounded by the outer-most termini of the outer slots which contribute to the hinge function.

In examples described herein, the hinge section varies in flexibility across the hinge. For example, when considering different positions across the hinge in a plane of the clip, for example where the jaws of the clip move with respect to each other in the plane of the clip, the flexibility of the hinge at one point may be different than the flexibility of the hinge at another point. In several examples herein of a hinge section, the hinge section is formed with a slot or other extended opening through the material of the clip where proximal portions of the jaws are joined. When the clip is in a relaxed open state, the opening has a profile or cross-sectional configuration, for example in the plane of the clip.

Where the profile of the opening is noncircular, the flexibility of different portions of the hinge segment will be different as a function of location in the hinge segment. For example, a portion of the opening defined by relatively thin walls will be more flexible at that portion than at another portion of the opening defined by thicker walls.

In one example, the hinge section 103 is asymmetric relative to the jaws. "Asymmetric" in the context of hinge section 103 being asymmetric relative to the jaws in FIGS. 3A and 3B, is that the hinge section, when positioned relative to the adjacent connection portions between the hinge section and the jaws (in the example of FIGS. 3A-C the dorsally and ventrally extending jaw portions), is asymmetric relative to a curving interface line at the location that the curving interface line intersects the hinge section 103. The curving interface line is defined by positions equidistant from the jaw surfaces when the jaws are in contact with each other and the curving interface line extends to the hinge section 103. Additionally, in the present example, the hinge section 103 separates the clip into two jaws and if a vertical (as seen in FIG. 4) line 200 divides the clip when in the closed configuration in half longitudinally, then the jaw sections adjacent the hinge section are unequal in mass, and the top jaw section in the example of FIG. 3 (part of top jaw 101) is lighter in mass than the bottom jaw section (part of bottom jaw 102). Also, as seen in FIG. 4, more of the opening 108 is on the lower jaw side than on the upper jaw side.

The hinge section 103 connects the proximally-extending sections of the top jaw member 101 and bottom jaw member 102 at respective angularly-extending elements in the form of dorsally- and ventrally-extending jaw elements 101H and 102V, respectively, through an elbow 103A, so that the hinge section 103 is offset from the top jaw member 101 and the bottom jaw member 102. The dorsally- and ventrally-extending jaw elements 101H and 102V extend at an angle to the average direction in which their respective jaws extend. In the examples herein, the jaw elements 101H and 102V are relatively rigid, compared to the hinge section 103, and may be formed from the same material as their respective jaw members. In these examples, the jaw elements 101H and 102V have the same flexibility as that of the jaw members. The hinge section 103 comprises a slot 108 that extends through the width of hinge section 103 (and in the present example extends laterally to openings on opposite sides of the hinge section 103), an inner hinge surface 109, and an outer hinge surface 110.

Slot 108 in one example extends longitudinally, for example between the inner hinge surface 109, and the outer hinge surface 110. In one example, the slot in saggital section (for example, a section parallel to the plane of the drawing of FIG. 1) is longer than it is wide, and may be somewhat elliptical or other selected shapes when extended to be straight, though in a resting or relaxed state the slot will take the configuration such as that shown in the drawings, such as FIG. 1 or 14. When incorporated as part of the hinge section 103, the slot will generally have an arcuate configuration, and will be configured to achieve the desired closing motion such as those described herein. Other slot configurations and closing motions are possible as well.

Slot 108, in the present example, is preferably positioned closer to inner surface 109 than to outer surface 110 to provide greater flexibility of the wall adjacent the inner surface 109 when the top jaw member 101 and bottom jaw member 102 are closing together, but it is understood that it can be substantially centered between the inner and outer hinge surfaces, or closer to the outer hinge surface than to the inner hinge surface, depending on the effect and motion desired. In the present example, the thickness 109A of the wall between the slot 108 and the inner surface 109 is less than the thickness 110A between the slot 108 and the outer surface 110. The adjacent wall along the inner surface 109 of the hinge section 103 may comprise a constant wall thickness (i.e., thickness 109A is substantially constant) or a varying wall thickness (i.e., thickness 109A varies over the arc length defining the extent of the slot 108 between the dorsally and ventrally extending jaw elements). In the case of a varying wall thickness, the thinnest section of the wall along the inner surface 109 may define the bending point or pivot point CL (FIGS. 3B & 3C) of the hinge when jaw members 101 and 102 are closing together, for example the arcuate position of the bending point relative to the slot 108, and in the present example within the slot 108.

Figure 3C:
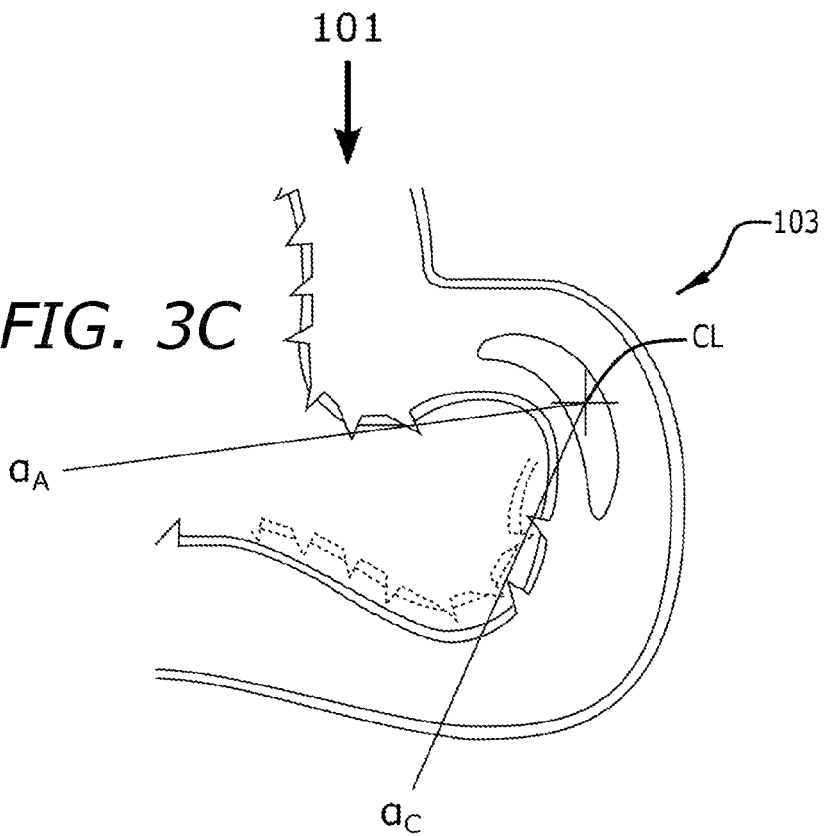
Figure 4:
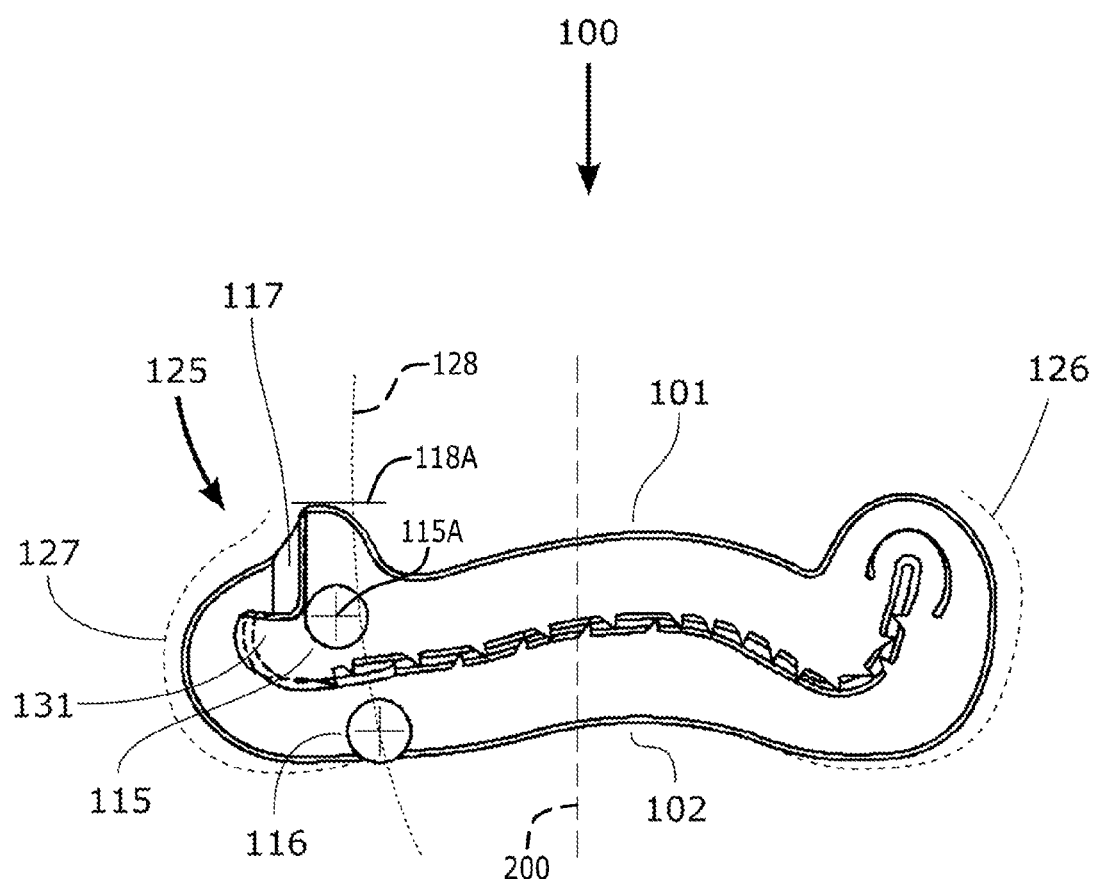
FIG. 4 is a side view of the surgical ligating clip of FIG. 1 in the closed position.
Figure 9:
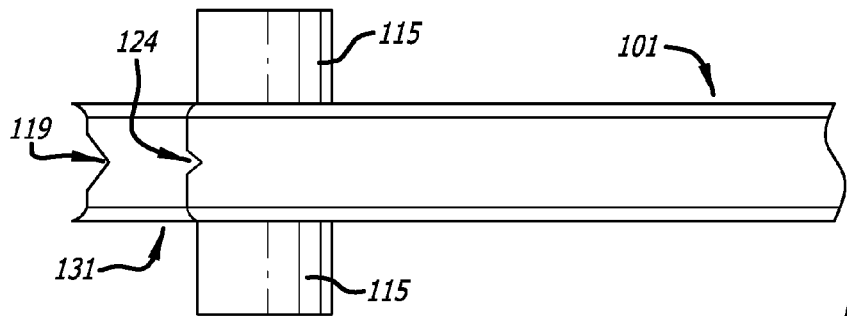
FIG. 9 is a top plan view of a distal portion of a top jaw in the clip of the example shown in FIG. 1.
Figure 10:
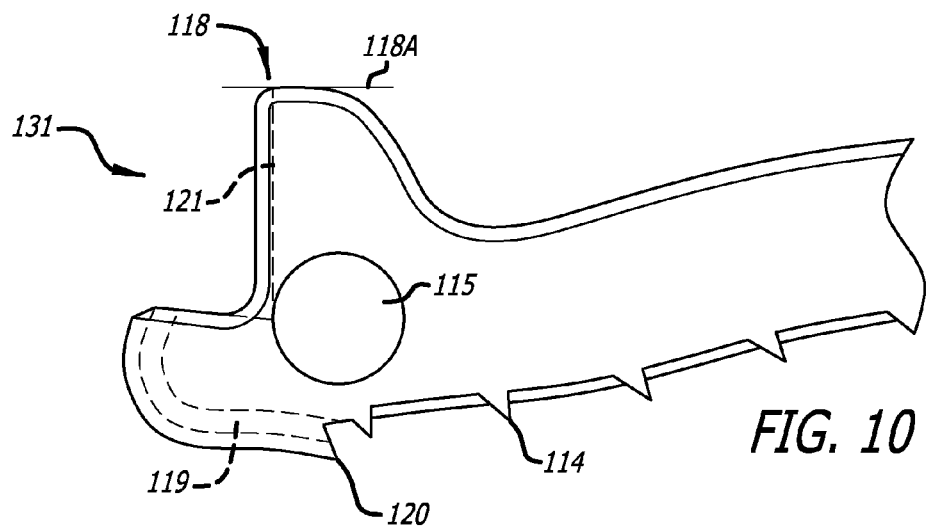
FIG. 10 is a side elevation of the portion shown in FIG. 9.
Figure 11:
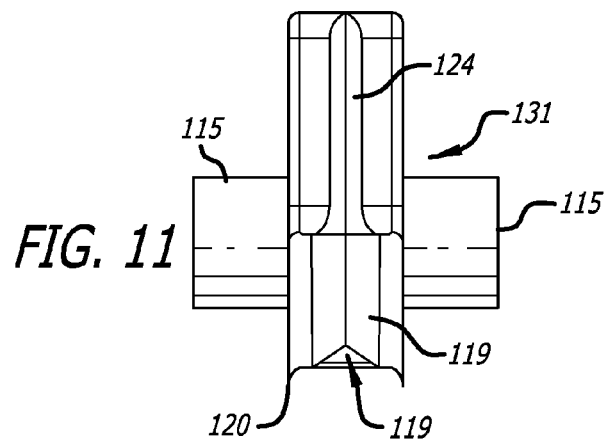
FIG. 11 is a front elevation view of the portion shown in FIG. 10.
Figure 12:
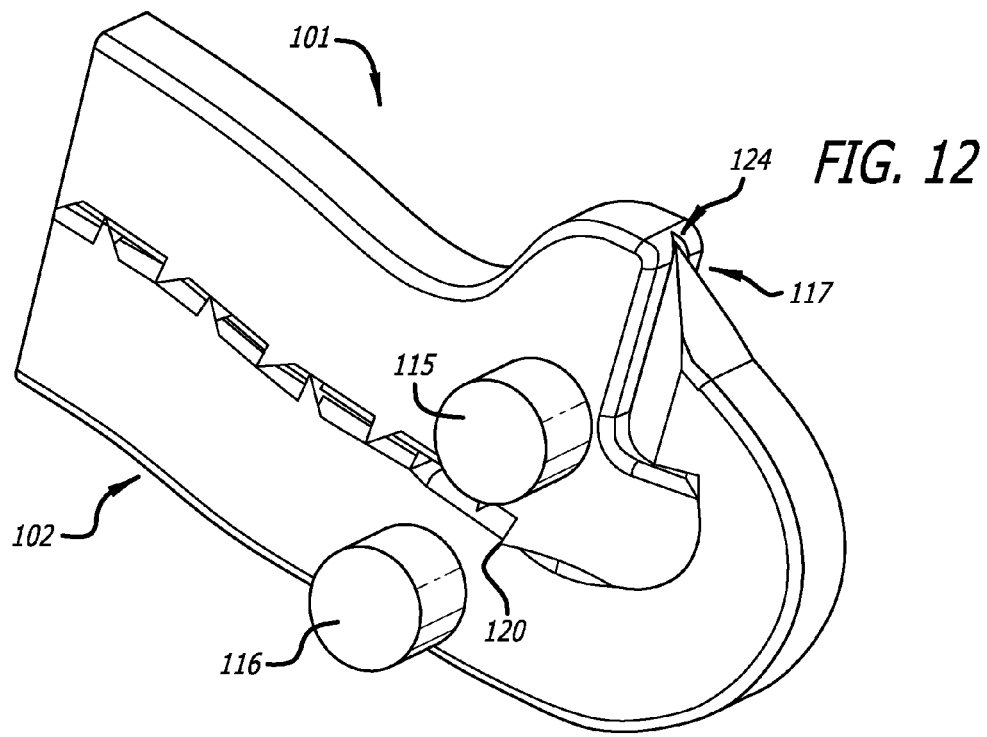
FIG. 12 is an isometric view of a distal portion of the clip of FIG. 1 shown in a closed configuration.
Figure 13:
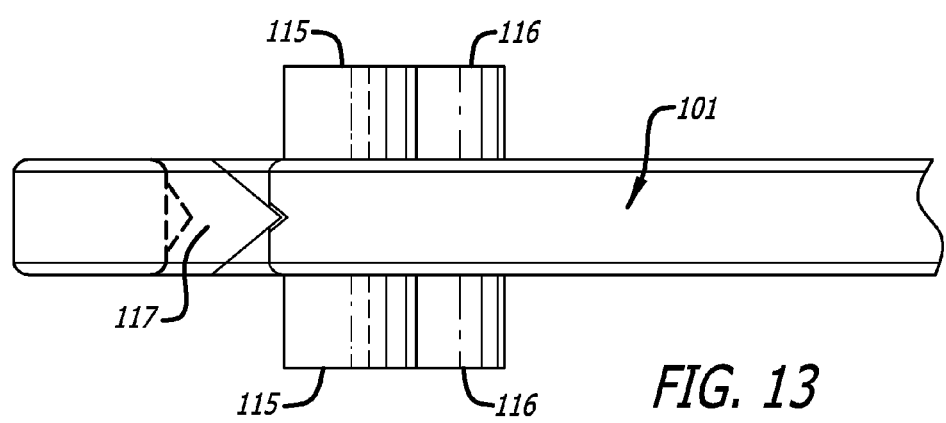
FIG. 13 is a top plan view of the portion shown in FIG. 12.

In the present example shown in FIGS. 3A-C, the thinnest section of the wall along the inner surface 109 is substantially centered along the arcuate extent of the slot 108. In other examples, the thinnest section of the wall along the inner surface 109 is measurably closer to the dorsally extending jaw element, and in other examples, the thinnest section of the wall along the inner surface 109 is measurably closer to the ventrally extending jaw element. Herein, "substantially" in the context of substantially centered is defined to be providing substantially the same hinge motion for a given clip and applier combination with substantially the same final jaw positions relative to each other, as a clip wherein the thinnest section of the wall along the inner surface 109 is precisely centered in the arcuate extent between the dorsally extending and ventrally extending jaw elements. "Not substantially" in the context of not substantially centered is defined to be not providing substantially the same hinge motion for a given clip and applier combination with substantially the same final jaw positions relative to each other, as a clip wherein the thinnest section of the wall along the inner surface 109 is precisely centered in the arcuate extent between the dorsally extending and ventrally extending jaw elements.

Having the inner wall thickness 109A less than that of the outer wall provides preferential bending or flexing of the inner wall relative to the bending or flexing of the outer wall. The preferential bending provides a measure of control over how the proximal portions of the jaws come together as the applier (not shown with FIGS. 3-4, but see the applier with respect to FIGS. 14-18) closes the jaws. Changing the inner and/or outer wall thicknesses can be achieved by keeping the slot 108 profile constant and moving the slot closer to or further away from the inner surface 109. Alternatively or additionally, the inner and/or outer wall thicknesses can be modified by changing the slot 108 profile. For example, the radius defining the inner surface 108A (e.g. radius defining the curved surface) of the slot 108 can be increased or decreased to change the wall thickness 109A. Likewise, the radius defining the outer surface 108B can be increased or decreased to change the wall thickness 110A, either separately or in addition to changing the radius defining the inner surface 108A. Similarly, these radii can be varied as a function of arcuate position to vary the respective thicknesses of the segments they define as a function of arcuate position. Additionally, having the pivot point CL positioned within the opening 108 (when the clip is in the open position such as shown in FIGS. 3A-C) may also help to provide a desired preferential bending. Other bending configurations may be achieved by positioning the pivot point CL within the inner wall or exterior (between the jaws) to the inner wall, or within the outer wall or exterior (outside the jaws) to the outer wall.

As can be seen in FIG. 3A, the wall thickness 109A is constant over a relatively short arc length compared to the arc length over which the outer wall thickness 110A is constant, in the present example. The wall thickness 109A, also can be varied as a function of radial position, or arcuate position along the inner surface 108A. Varying the wall thickness 109A will also vary the profile of the inner wall 108A. Likewise, the wall thickness 110A can be varied as a function of radial position, or arcuate position along the outer surface 110A. Varying the wall thickness 110A will also vary the profile of the outer wall 108B.

The outer wall thickness 110A is substantially constant over the arcuate extent of the slot 108 in the example shown in FIGS. 3A-C. Therefore, the thickness 110A of the wall between the slot 108 and the outer surface 110 is substantially the same between the dorsally extending jaw element 101H and the ventrally extending jaw element 102V. In this example specifically, the intermediate, approximately 75% of the wall between the slot 108 and the outer surface 110 has substantially the same thickness, while the thickness at the end portions of the slot 108 increase, for example to allow the endpoints of the slot 108 to have a curvature. As used herein, "substantially" in the context of substantially constant thickness 110A of the outer wall is a wall thickness of the outer wall that is constant over at least 50% of the outer wall over the extent of the slot or opening 108. In the case of a varying wall thickness of the outer wall 110, the thinnest section of the wall along the outer surface 110 may help to define the pivot point CL, and in one example a center point or intermediate point of the thinnest section of the wall on the outer surface 110 may be aligned with the pivot point CL and the thinnest section of the wall on the inner surface 109. In other examples, the center point or intermediate point of the thinnest section of the wall on the outer surface 110 may be un-aligned with the pivot point CL and the thinnest section of the wall on the inner surface 109.

The ventral jaw section 102V of the bottom jaw member 102 further comprises a plurality of teeth 111 located on inner surface 109. In the present example, an axis (not shown) bisecting a respective tooth 111 is positioned at an angle to a line normal to the surface to which the tooth is attached (in other words, off perpendicular). Also in the present example, the axis is angled toward the top jaw member 101, as opposed to the bottom jaw member. This angle helps to reduce the likelihood that tissue will migrate along the surface to which the tooth is attached toward the bottom jaw member 102. This angle also helps to reduce the resistance to tissue movement/ingress into the cavity toward the inner surface 109 when the tissue is placed into the clip and/or as the clip is being closed. As with any individual tooth described or illustrated herein, the angle of the axis bisecting the tooth (when viewed from the side such as in FIGS. 1, 3-5) can be selected to increase the ability of the tooth to resist tissue movement/egress out of the clip or out of the area in which the tooth is located.

Referring to FIG. 3B, closing the top jaw 101 and/or the bottom jaw 102 initiates the rotation of the top jaw 101 around the imaginary pivot point CL (FIGS. 3B and 3C) relative to the bottom jaw 102. (In the present discussion, CL is the point of intersection of all lines through respective points on the top jaw 101 when the jaw is open (FIG. 3B) and when the jaw is closed (FIG. 3C).) The angular position of heel 121 relative to the bottom jaw decreases from angle $\alpha_A$ to $\alpha_B$ relative to the origin $\alpha_C$, or the line when the clip is in the closed position. At angular position $\alpha_B$, heel 121 is at a position closer to the inner surface 107 of the bottom jaw member 102 while the opening at the distal end of the jaw members 101 and 102 remains wider (see for example FIG. 5B). The closing of heel 121 against or closely adjacent the inner surface 107 (and/or proximally relative to the hinge section 103) causes the vessel or tissue to be securely engaged against the inner surface 107 or pinched between the adjacent surfaces of the top and bottom jaws, reducing the likelihood of the tissue or vessel slipping out of the clip 100 as the jaws are closed and locked in place (locked together). Additionally, the teeth 114 around the perimeter of the heel 121 help to keep the tissue or vessel from slipping out of the clip, or at least distally. The teeth 114 also help retain the tissue or vessel based on an angular orientation of the bisecting axis directed proximally (positioned at an angle to a line normal to the surface, for example 107B shown in FIG. 7, to which the tooth is attached (in other words, off perpendicular in a proximal direction). The action of continuing to close the jaws creates further rotation or angular movement of the heel 121 towards the proximal side of the clip 100, dragging or pulling the tissue or vessel proximally. At angular position $\alpha_C$, the jaw members 101 and 102 are fully closed.

The relative position of CL, as shown in FIG. 3B, has been found to be useful. In this context, CL is approximately centered between the inner and outer walls 108A and 108B, and is approximately centered along an arc between the ends of the slot 108 (as seen in FIG. 3B), when the slot 108 is positioned horizontally and vertically (when viewed as shown in FIG. 3B) as shown. The slot 108 starts approximately vertically at the vertical (as viewed in FIG. 3B) leg 102V extending ventrally from the rest of the bottom jaw 102. The slot extends in an arc along a hinge leg 103V to a horizontal hinge leg 103H (as viewed in FIG. 3B) and terminates approximately horizontally, extending into the adjacent horizontal portion 101H of the top jaw 101. Other configurations of the slot and its position in the hinge section 103 can be used to achieve the desired hinge or pivoting action and movement of the heel 121 and closure of the spacing 121A. Another example of a hinge location and configuration is shown in FIGS. 14-18, discussed more fully below.

The junction of the horizontal leg 101H and the adjacent proximal portion of the top jaw 101 forms the heel 121. The surface configuration of the inner portion of the heel 121 can also affect the rate of closure of the spacing 121A. (Rate in the context of movement of the heel 121 and decrease in the spacing 121A is defined below.) If the curvature of the inner surface 109 at the horizontal leg 101H is more concave than as shown in FIG. 3B, the heel 121 will be protruding into the cavity defined by the inner wall 109. If more concave, the wall thickness 109A may be smaller resulting in a higher rate of closure of the spacing 121A. Additionally, if the curvature of the heel 121 is eccentric (as opposed to substantially semi-circular as shown in FIGS. 3A-C but for the teeth), the point of eccentricity and its position along the heel 121 may also affect the rate of closure or decrease of the spacing 121A. These aspects of the heel configuration can be modified as desired to produce the desired effect on tissue in the cavity when the jaws are closing.

In addition to the heel configuration, other parts of the clip configuration can be modified to affect how the clip operates. For example, the length of the vertical leg 102V can be increased while keeping the overall slot position the same, thereby increasing the spacing 121A, if all other parameters remain the same. Additionally, the length of the horizontal leg 101H can be increased while keeping the overall slot position the same to increase the size of the cavity in the hinge area for receiving tissue. Alternatively, or additionally, the legs 101H and/or 102V can remain constant while moving the position of the slot 108, such as is illustrated in the configuration of FIGS. 14-18 closer to the top jaw, which may also be considered shortening the horizontal leg 101H and lengthening the vertical leg 102V, or closer to the bottom jaw (not shown).

As the closing of the jaws brings the heel 121 closer to the inner surface 107, the spacing 121A (FIG. 3B) decreases. The rate at which the spacing 121A decreases may be determined at least in part by the position of CL. In this context, "rate" means the rate of closure or decrease in spacing 121A relative to the angular rate of closure of the top and bottom jaws. For example, positioning CL higher within the slot 108 (but still centered between the inner and outer walls 108A and 108B, respectively) would decrease the rate of closure of the spacing 121A. This is because CL is positioned more distally and also ventrally from the bottom jaw 102. Positioning CL lower within the slot 108 (but still centered between the inner and outer walls 108A and 108B, respectively) would increase the rate of closure. The rate of closure will also be affected by the thickness 109A of the wall between the slot 108 and the inner wall surface 109. Other factors may also be used to adjust or modify the rate of closure. For example, thickness of the tissue that may be inserted between the heel 121 and the surface 107 may change the decrease in the spacing 121A. In one configuration, the distance 121A is brought to its minimum before the jaws are closed and locked. In one configuration, the heel 121 is positioned and configured to have a relatively short distance of travel to the bottom jaw 102, while having a relatively wide initial starting spacing when the top and bottom jaws are open for more easily receiving tissue into the cavity (adjacent the inner surface 109). Such a configuration is made more easy with a higher rate of closure.

Top jaw member 101 further comprises a distal section 112 that may have a latching feature. The latching feature at distal section 112 comprises shroud 118, a groove 119, and latch 131 (FIGS. 1-2). Shroud 118 is configured to extend above the outer surface 104 to a height that at least matches the tip of the piercing element 117 when the clip is in a closed and locked position. Shroud 118 may comprise a channel 124 where the piercing element 117 may engage when the top and bottom clip jaw members 101 and 102 are closed and locked in place. Groove 119 faces outwardly of and extends proximally from the face of the latch 131 continuing towards the inner surface 105. Tooth pair 120 (which may resemble a fang) may be provided at the distal end of inner surface 105 and may be configured such that it has facing surfaces defining an edge that generally extends and points towards the bottom jaw member 102. The tooth pair 120 may be configured to be sharp enough to puncture tissue in conjunction with the piercing element 117 described below. A pair of laterally-extending cylindrical bosses 115 located adjacent the distal section 112 may be provided on both sides of top jaw member 101, for example to be complimentary to respective surfaces on an applier used to apply the ligating clip.

Bottom jaw member 102 comprises a distal section 113 that may have a piercing feature and a latching feature configured to mate with the latching feature of the top jaw member 101. Distal section 113 comprises a piercing element 117 having a tip 117A disposed opposite latch 123. The piercing element 117 is generally configured such that it extends to a narrow portion or point that is facing or pointed towards the top jaw member 101. The piercing element 117 may be configured to be sharp enough to puncture tissue during normal use. A pair of laterally-extending cylindrical bosses 116 located adjacent the distal section 113 are provided on both sides of bottom jaw member 102, for example to be complimentary to respective surfaces on an applier used to apply the ligating clip.

In one example, the piercing element 117 is narrowed or pointed with a tip sufficient to puncture tissue during normal use. The piercing element may be a pointed bevel, cone, trapezoid shape or other shape providing the desired tip geometry. The geometry may have two or more faces or sides in which an inclusive angle of opposing faces or sides is 150° or less (for example, as shown in FIGS. 14-18), but an angle of 90° or less increases the ease with which tissue can be punctured with the piercing element, while an angle of 60° or less provides an even sharper piercing element. For example, any one, two or three of the angles $\alpha 1$, $\alpha 2$, and $\alpha 3$ (FIGS. 6-8) can be configured to have the angles recited. Additionally, the piercing element may have a durometer of at least 50 Shore D in order to provide a sufficient hardness to puncture the tissue. Other piercing element configurations can also be used to produce a tip sufficient to puncture tissue during normal use. The piercing element 117 may be an integral part of the whole clip structure as discussed in these examples such that the ligation clip 100 is only made from a single material. Alternatively (not shown), to further strengthen and provide a more effective and durable piercing element 117, it may be constructed from different materials including but not limited to metals like stainless steel, titanium, nickel titanium, gold, platinum, cobalt, chromium, and the like, or non metal including plastics with increased hardness properties as compared to the material used to make the remaining clip. The piercing element 117 may be assembled or connected to the distal section of the bottom jaw 102 (not shown) by means of methods commonly known in the art such as adhesive bonding, insert molding, ultrasonic welding, hot melt, and the like. Yet another alternative means to strengthen the structure of the piercing element 117 is by coating or plating the surface (not shown) with a metallic material commonly known in the art such as gold, platinum, chrome, nickel, or the like or with a harder grade of polymeric material using processes also commonly known in the art.

Inner surfaces 105 and 107 may further comprise a plurality of teeth 114. It should be noted that the teeth 114 and 111 (FIGS. 1-3C) may be configured with other orientations and shapes that enable effective securement of a vessel or tissue when the clip is closed in the locked position. These alternative configurations may include, but are not limited to, domes, pyramids, bosses and notches, tongue(s) and groove(s), similar features, and/or combinations thereof. Additionally, as noted herein, any one tooth (or more than one tooth) can be configured such that a bisecting axis is oriented at an angle to the surface supporting the tooth (or at an angle to a line running parallel to the surface supporting the tooth). In the example illustrated, all (and therefore a majority) of the teeth have their bisecting axes (for example 114A in FIG. 7) angled in a proximal direction, or in such a direction that reduces the possibility of tissue moving distally or outward of the clip or along a surface of a jaw in a direction that would lead to the tissue moving outward of the clip.

In addition to variations or modifications in individual teeth, frequency or spacing or other relative attributes of multiple teeth can be selected as desired. For example, the number per unit length of teeth 114 on the bottom jaw 102 is relatively uniform, while that on the top jaw 101 varies over the length of the top jaw. In another example, each tooth can extend the entire width of the jaw, or beyond, or can extend less than the entire width. For example of less than the entire width, a tooth can extend only half way across the width of the jaw. Moreover, every other or every second tooth can extend halfway inward from one side while the remaining teeth on a jaw can extend halfway inward from the other side (alternating). Additionally, on the top jaw, the linear density is higher at a proximal portion of the jaw than at a distal portion of the jaw. Furthermore, the teeth configuration (i.e. any feature described herein with respect to a given tooth or combination of teeth) on one jaw can be different than the corresponding teeth configuration on the immediately adjacent portion of the opposite jaw, when the jaws are closed. For example, as depicted in FIG. 3C and FIG. 4, there are at least two teeth on the top jaw that do not have a corresponding tooth from the lower jaw extending between them. As seen in FIG. 4 in the present example, there are seven teeth in the top jaw that do not have any teeth extending between them from the bottom jaw.

In the example illustrated, one jaw has a length of surface without any teeth and the other jaw has a similar length of surface facing it that has two or more teeth. As noted above in the present example, the bottom jaw has a length of surface 107A (FIG. 1) where the facing surface on the top jaw has seven teeth. In this configuration, the bare surface 107A is configured to allow tissue to move along it relatively freely relative to the opposite surfaces on the other jaw. For example, where the heel 121 is closely adjacent the bottom jaw, and the bare surface 107A, movement of the top jaw and the adjacent teeth on the heel 121 and grab and move tissue into the cavity adjacent the inner surface 109 while the tissue slides along the surface 107A. As the heel 121 moves into the cavity, other teeth on the top jaw move into position opposite the surface 107A. This configuration promotes grabbing and pulling the tissue into the cavity.

Also in the example illustrated, the smooth surface 107A is bordered on both sides (proximally and distally) by one or more teeth. The length of the smooth surface 107A is greater than at least twice the smallest spacing between adjacent teeth on the clip. Additionally, when the jaws are facing each other, such as when the clip is closed, at least two teeth from the top jaw are positioned opposite the smooth surface 107A without an intervening tooth on the bottom jaw. Other configurations are also possible.

It should also be noted that while cylindrical bosses 115 and 116 are depicted as externally projecting features in these figures, it is also contemplated that low-profile bosses or recesses such as those described in U.S. Pat. Publication US20090088783, incorporated herein by reference in its entirety, may be employed to facilitate placement of clips such as those described herein about a target vessel when used with a complementary applier.

FIG. 4 is a side view of an example of the inventions depicted in FIGS. 1-3 in the closed position. When ligation clip 100 is closed, piercing element 117 is fully embedded within channel 124 of shroud 118, forming atraumatic surface 125. Additionally, the tip 117A is at or below (as viewed in FIG. 4) a tangent line 118A to the shroud 118 (see FIG. 4). In this manner the tip of the piercing element 117 is not exposed to adjacent tissue that may potentially be lacerated, cut, severed, or serrated by the sharp edges and/or points of the piercing element 117. Piercing element 117 embedded within channel 124 also serves as a locking feature that prevents or limits latch 131 from sliding or disengaging sideways or laterally during normal operation.

In addition to the atraumatic surface 125, the remaining external surfaces of ligation clip 100 do not have any sufficiently sharp or pointed features that may catch, tear, or lacerate surrounding tissues.

Closing of the jaw members 101 and 102 is accomplished with the aid of a clip applier (FIGS. 14-18, the same reference numerals are applied to parts that are the same as previously described herein), where the pair of cylindrical bosses 115 and 116 of clip 100A are mounted in the applier jaws (132 and 133). As the jaw members 101 and 102 are closed to a position where the tip of the piercing element 117 comes in contact with the adjacent portion of the groove 119 (see also FIG. 16), the proximal side of bottom jaw member 102 and the adjacent hinge section 103A (leg 103V) are forced to deflect outward as depicted by the imaginary line 126 (FIG. 4), storing energy into the deflected segment. The distance between the centerline 115A of the cylindrical boss 115, and applier jaw imaginary arc-shaped path 128 controls the amount of outward deflection 126. The imaginary path 128 is the track followed by the cylindrical boss 115 and 116 when they are held in the applier jaws, thus the top jaw member 101 shifts proximally, causing the proximal side of bottom jaw member 102 and the adjacent hinge section 103A to deflect outward (compare FIGS. 16 and 17). As the applier further closes the clip 100A, the distal side of bottom jaw member 102 deflects outward as depicted by the imaginary line 127 (compare FIGS. 16 and 17). The deflection is a result of the piercing element 117 sliding outwards or distally along the groove 119. Once the clip is closed and the mating latches 131 and 123 are engaged, the inner, proximally-facing surface or edge 1178 (FIG. 1) at the distal portion of the bottom jaw member 102 rests in or is embedded within the proximally-facing groove 124, preventing or limiting the latch 131 from sliding or disengaging sideways or laterally during normal operation. Upon release of cylindrical bosses 115 and 116 from the applier jaws 132 and 133, the proximal side of the bottom jaw member 102 which had deflected outward during closing of the applier jaws (as shown by the imaginary line 126) deflects distally as the stored energy of the deflected segment is simultaneously released. The final closed and locked state of clip 100 after full release from the applier jaws results in the top jaw member 101 shifted distally with the mating latches 131 and 123 fully engaged as shown in FIG. 4.

Figure 14:
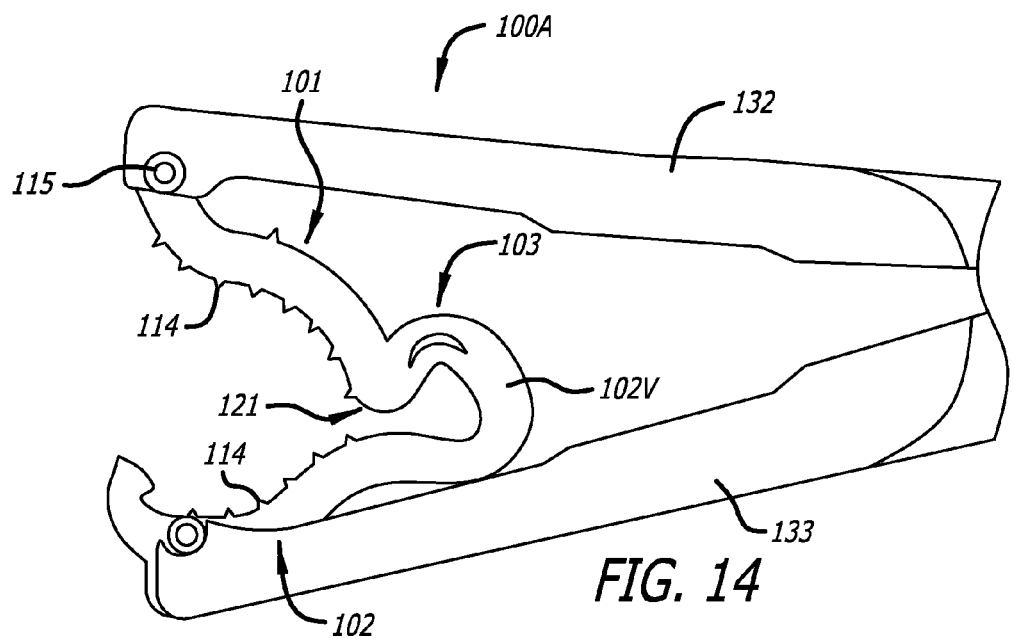
FIG. 14 is a photograph of a side elevation of an example clip in the jaws of an applier with the clip in an open configuration.
Figure 15:
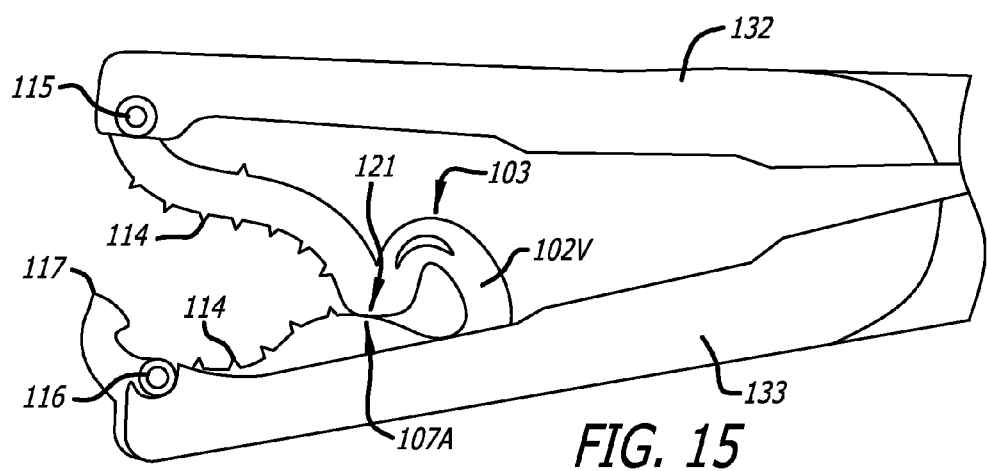
FIG. 15 is a photograph of a side elevation of the clip of FIG. 14 in the jaws of an applier with the clip in a partially closed configuration with two parts of the clip jaws in contact.
Figure 16:
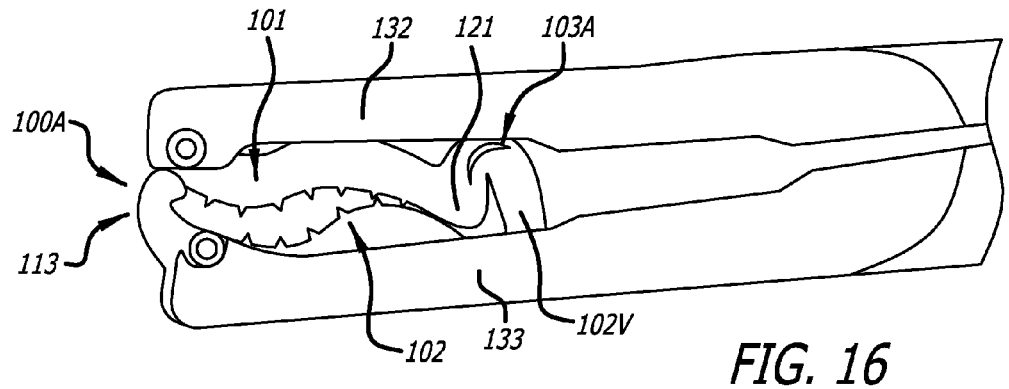
FIG. 16 is a photograph of a side elevation of the clip of FIG. 14 in the jaws of an applier with the clip further closed and distal portions of the clip jaws in contact.
Figure 17:
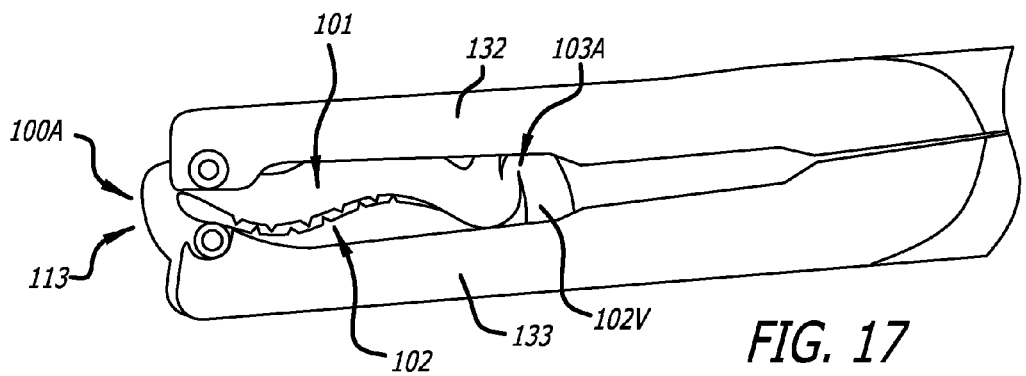
FIG. 17 is a photograph of a side elevation of the clip of FIG. 14 in the jaws of an applier with the clip almost closed.
Figure 18:
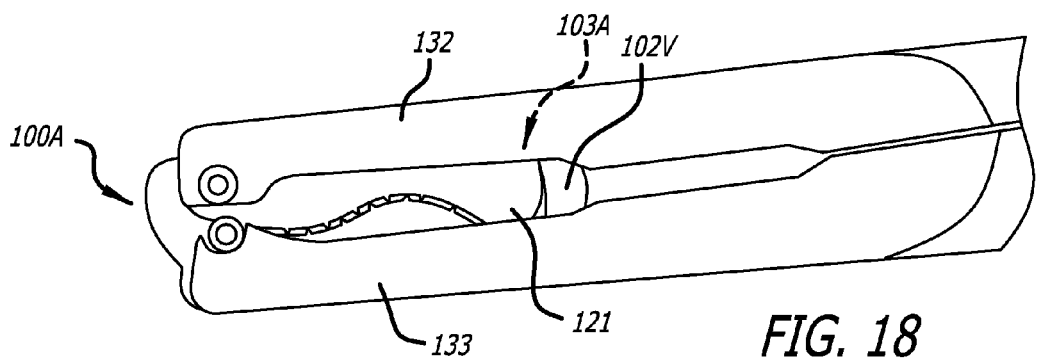
FIG. 18 is a photograph of a side elevation of the clip of FIG. 14 in the jaws of an applier with the clip fully closed.

FIG. 5 is a series of schematics (5A-5D) depicting the placement and closure of the ligation clip 100 about a target vessel 129, and FIGS. 14-18 show the use of a ligation clip in conjunction with an applier for closing the ligation clip. In the illustrated example, target vessel 129 further comprises extraneous tissue 130 (e.g. connective tissue, fat, fibrous scar tissue, etc.) that would traditionally hinder or prevent the closure of ligation clips known in the art. FIG. 14 shows a fully open clip positioned in the jaws of an applier and FIG. 5A shows the ligation clip 100 approximated about the target vessel 129 in a fully-open configuration. The heel 121 at a proximal portion of the first jaw is spaced apart from the second jaw 102, but closer to the second jaw than a distal portion of the first jaw, for example that portion including bosses 115. Upon closing the top jaw member 101 and bottom jaw member 102, the teeth 114 on the inner surfaces 105 and 107 engage and grip the surface of target vessel 129. FIG. 5B and FIG. 15 show ligation clip 100 in a semi-closed state. The teeth 114 on inner surface 107 of jaw member 102 secure the base of the target vessel 129 in place while the pivoting motion of jaw member 101 about hinge section 103 (or 103A in FIGS. 14-18) causes the teeth 114 disposed around the heel 121 on inner surface 105 to engage against and pull the upper surface of target vessel 129 towards the inner surface 109 of hinge section 103/103A. The heel 121 and the teeth on the surface thereof move proximally the tissue along the smooth surface 107A of the bottom jaw member 102. The piercing element 117 begins to engage extraneous tissue 130. FIG. 5C and FIGS. 16-17 show the ligation clip 100 in an almost completely closed state. The teeth 114 disposed around the heel 121 on inner surface 105 have pulled the target vessel 129 towards inner surface 109 of hinge section 103/103A to the extent that the teeth 111 resident on inner surface 109 have engaged the target vessel 129 and secured the target vessel 129 within hinge section 103/103A. In this position, piercing element 117 has penetrated extraneous tissue 120, enabling the engagement of latch 131 and latch 123 as ligation clip 100 is closed. FIG. 17 shows the distal section 113 of the second jaw 102 flexing outward or distally, as well as a portion of the hinge section 103 flexing proximally. FIG. 5D depicts ligation clip 100 fully closed about target vessel 129, with piercing element 117 fully penetrating the extraneous tissue 130. FIG. 18 shows the ligation clip 100 fully closed, with the heel 121 fully within the cavity and the hinge section 103A fully flexed (hinge section 103 would be analogous) and the latching mechanism 123 and 131 fully engaged.

In the clip shown in FIGS. 14-18, hinge section 103 in this example is asymmetric relative to the jaws. As see most clearly in FIG. 18, when positioned relative to the adjacent connection portions between the hinge section and the jaws and the jaws are closed, the hinge section is asymmetric relative to a curving interface line at the location that the curving interface line intersects the hinge section 103. The curving interface line is defined as above with respect to FIGS. 3A-3C. In the example shown in FIG. 18, there is more of the opening 108 on the top jaw side than on the bottom jaw side. Additionally, in the present example, the hinge section 103 separates the clip into two jaws and if a vertical line similar to the vertical line 200 in FIG. 4 divides the clip when in the closed configuration in half longitudinally, then the jaw sections adjacent the hinge section are unequal in mass, and the top jaw section in the example of FIG. 3 (part of top jaw 101) is lighter in mass than the bottom jaw section (part of bottom jaw 102).

The ligation clip 100 may be made of a metallic or non-metallic biocompatible material including, but not limited to stainless steel, titanium, acetal, polyethylene, nylon, peek, Teflon, polycarbonate, alloys or combination thereof, and the like suitable for a long term or permanent implant. Polymer materials may be non-resorbable (i.e. permanent implant) or resorbable (i.e. degrades over a period of time).

The ligation clip 100 may be made in various sizes to allow ligation of different sizes of vessel or tissue. All design features, clip functionality, and methods of use and operation described within the details of this disclosure remain applicable to the other sizes. These various sizes of ligation clips can respectively be used to ligate a variety of vessel sized, with the largest diameter of about 16 mm.

Having thus described several exemplary implementations, it will be apparent that various alterations and modifications can be made without departing from the concepts discussed herein. Such alterations and modifications, though not expressly described above, are nonetheless intended and implied to be within the spirit and scope of the inventions. Accordingly, the foregoing description is intended to be illustrative only.

That which is claimed is:

1. A ligation clip comprising:
   first and second jaws having proximal portions and distal portions, the first and second jaws extending generally longitudinally and movably coupled to each other by a hinge portion at the proximal portions;
   a tip member on the distal portion of the first jaw;

a hook member on the distal portion of the second jaw, the hook member being configured to deflect around the tip member to secure the ligation clip in a closed configuration;

at least one first tooth positioned on the first jaw; and at least one second tooth positioned on the second jaw, wherein the first jaw includes a first convex segment between the tip member and the hinge portion, the second jaw includes a second convex segment between the hook member and the hinge portion, the at least one first tooth is positioned on the first convex segment, the at least one second tooth is positioned on the second convex segment, and the first and second convex segments are configured to pinch a proximal portion of tissue while the distal portions are spaced apart.

2. The ligation clip of claim 1, wherein the at least one first tooth includes a plurality of first teeth, each extending at an angle from an inner surface of the first jaw.

3. The ligation clip of claim 2, wherein the at least one second tooth includes a plurality of second teeth, each extending at an angle from the inner surface of the second jaw.

4. The ligation clip of claim 1, wherein the at least one first tooth includes a plurality of first teeth, a first density of the first teeth on a first portion of the first jaw is greater than or equal to zero, and a second density of the first teeth on a second portion of the first jaw is greater than the first density.

5. The ligation clip of claim 1, wherein the at least one first tooth includes a plurality of first teeth, the at least one second tooth includes a plurality of second teeth, and the plurality of first teeth has a different density than the plurality of second teeth.

6. The ligation clip of claim 1, wherein one of the first and second jaws comprises an upper jaw, and the proximal portion of the upper jaw has a greater density of teeth than the distal portion of the upper jaw.

7. The ligation clip of claim 1, wherein at least one of the first and second jaws includes a portion having a smooth surface with a length greater than at least twice a smallest length between adjacent teeth.

8. The ligation clip of claim 1, wherein the at least one first tooth is positioned on a lateral extension of the first jaw.

9. The ligation clip of claim 1, wherein the at least one first tooth includes first and second teeth, and when the ligation clip is in a closed configuration, the second jaw has no teeth between the first and second teeth on the first jaw.

10. The ligation clip of claim 1, wherein the hinge portion includes a wall defining an opening.

11. The ligation clip of claim 10, wherein the wall has a length greater than a width.

12. The ligation clip of claim 10, wherein the hinge portion comprises a first portion and a second portion, the first portion having a flexibility different than a flexibility of the second portion.

13. The ligation clip of claim 10, wherein the opening extends through an arc of the hinge portion when the ligation clip is in an open configuration.

14. The ligation clip of claim 13, wherein a flexibility of the hinge portion at a center of the arc is greater than a flexibility of the hinge portion at an end of the arc.

15. The ligation clip of claim 13, wherein the opening is formed on a first side of a first wall having a first thickness and on a second side of a second wall having a second thickness, the second thickness being greater than the first thickness.

16. The ligation clip of claim 10, wherein the ligation clip includes a pivot point about which the first jaw pivots relative to the second jaw, and wherein the pivot point is positioned within the opening when the ligation clip is in an open configuration.

17. The ligation clip of claim 1, further comprising a first relatively inflexible, angularly-extending element extending between the hinge portion and the first jaw.

18. The ligation clip of claim 17, further comprising a second relatively inflexible, angularly-extending element extending between the hinge portion and the second jaw.

19. The ligation clip of claim 18, wherein the first and second angularly-extending elements extend at an approximately right angle relative to each other when the ligation clip is in an open, relaxed state.

20. The ligation clip of claim 1, wherein the first jaw includes a corner portion having an inner surface facing the second jaw, the inner surface of the corner portion being curved.

21. The ligation clip of claim 20, wherein the inner surface of the corner portion is partially circular.

22. The ligation clip of claim 20, wherein the inner surface of the corner portion has an eccentric curvature.

23. The ligation clip of claim 20, wherein the at least one first tooth includes a plurality of first teeth on the inner surface of the corner portion.

24. The ligation clip of claim 23, wherein at least one of the plurality of first teeth on the inner surface of the corner portion extends at least partly toward the hinge portion when the ligation clip is open and in a relaxed state.

25. The ligation clip of claim 1,
wherein the hook member includes a piercing element at a distal end portion of the second jaw, and the piercing element includes a longitudinally extending edge, and
wherein the tip member includes an edge receiver positioned on a distal end portion of the first jaw and configured to receive the longitudinally extending edge.

26. A method of applying a ligation clip to a tissue, the ligation clip including first and second jaws, each of the first and second jaws having a proximal portion, a distal portion, and a convex segment, the method comprising:
positioning the ligation clip in an open configuration, wherein the distal portions of the first and second jaws are spaced apart and the tissue is received between the first and second jaws;
pivoting at least one of the first and second jaws;
pinching a proximal portion of the tissue with the convex segments while the distal portions are spaced apart; and
pulling the pinched proximal portion of the tissue with the first jaw proximally along the second jaw.

27. The method of claim 26, further including moving the distal portion of the first jaw into contact with the distal portion of the second jaw.

28. The method of claim 26, wherein pulling the pinched proximal portion of the tissue includes pulling the pinched proximal portion of the tissue along an area of the second jaw without any teeth.

29. The method of claim 26, wherein pinching includes contacting the proximal portion of the tissue with at least one tooth positioned on the convex segment of the first jaw.

30. The method of claim 26, further including closing the ligation clip to reduce a spacing between the first and second jaws to a minimum.

31. The method of claim 26, further including deflecting a hinge portion as the distal portion of the first jaw moves along a distal portion of the second jaw.

32. The method of claim 31, wherein deflecting the hinge portion includes deflecting the hinge portion distally.

33. The method of claim 26, wherein pulling the proximal portion of the tissue includes moving the proximal portion of the first jaw proximally to pull the proximal portion of the tissue along the second jaw to an area adjacent a hinge portion joining the first and second jaws.

34. The method of claim 26, wherein pulling the proximal portion of the tissue includes moving the proximal portion of the first jaw proximally to pull the pinched proximal portion of the tissue toward a hinge portion joining the first and second jaws.

* * * * *